United States Patent [19]

Mazurek et al.

[11] Patent Number: 5,702,953
[45] Date of Patent: Dec. 30, 1997

[54] DEVICE FOR ANALYSIS OF RAPID AGGLUTINATION OF PARTICLES AND METHOD FOR USING SAME

[75] Inventors: Carol Mazurek, Elmhurst, Ill.; Charles L. Nelson, Richland, Mich.; Steven C. Hodges, Buffalo Grove; James W. Scheffel, Mundelein, both of Ill.

[73] Assignee: Abbott Laboratories, Abbott Park, Ill.

[21] Appl. No.: 893,964

[22] Filed: Jun. 4, 1992

Related U.S. Application Data

[63] Continuation of Ser. No. 818,410, Jan. 3, 1992, abandoned, which is a continuation of Ser. No. 572,519, Aug. 23, 1990, abandoned.

[51] Int. Cl.⁶ .................................................. G01N 33/86
[52] U.S. Cl. ..................................... 436/69; 422/73
[58] Field of Search ........................... 422/73, 99–102; 436/69

[56] References Cited

U.S. PATENT DOCUMENTS

| | | | |
|---|---|---|---|
| 3,492,096 | 1/1970 | Hattersby | 436/69 |
| 3,799,742 | 3/1974 | Coleman | 422/61 |
| 4,551,308 | 11/1985 | Mintz | 422/73 |
| 4,756,884 | 7/1988 | Hillman et al. | 422/81 |
| 4,775,515 | 10/1988 | Cottingham | 422/73 |
| 4,948,961 | 8/1990 | Hillman et al. | 422/73 |

*Primary Examiner*—Lyle A. Alexander
*Attorney, Agent, or Firm*—David L. Weinstein

[57] ABSTRACT

A device for particle agglutination analysis and a method for its use. The device includes means forming a longitudinally extending channel, an opening communicating from the exterior of the device to a first end of the channel, a reservoir communicating with the second end of the channel, and a vent opening communicating from the reservoir to the exterior of the apparatus. The channel has a sufficiently large cross section and the vent is positioned such that, when the channel is in a vertical position, a given amount of fluid, introduced through the opening into the channel will flow by gravity through the channel and into the reservoir, filling the channel to a desired height and the reservoir to the same height without flowing through the vent, while air escapes through the vent. Gravity causes sufficient movement of the particles so that agglutination may occur.

8 Claims, 4 Drawing Sheets

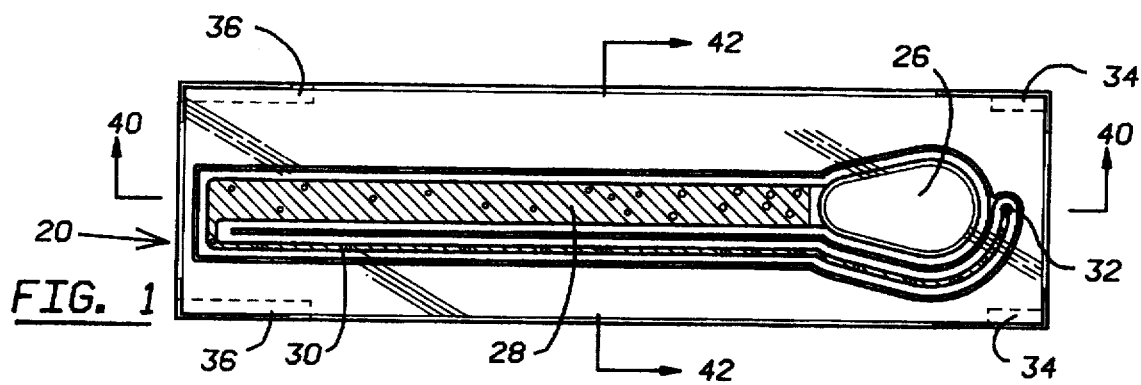
FIG. 1
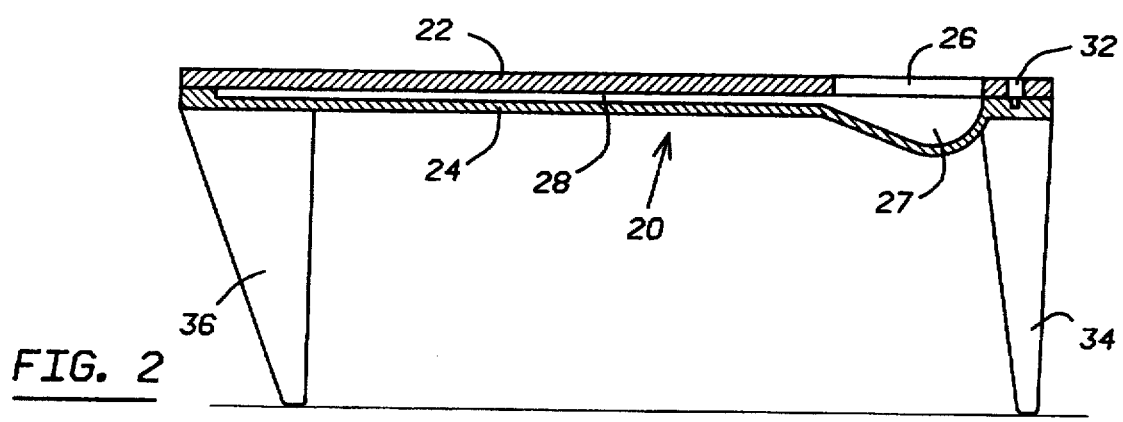
FIG. 2
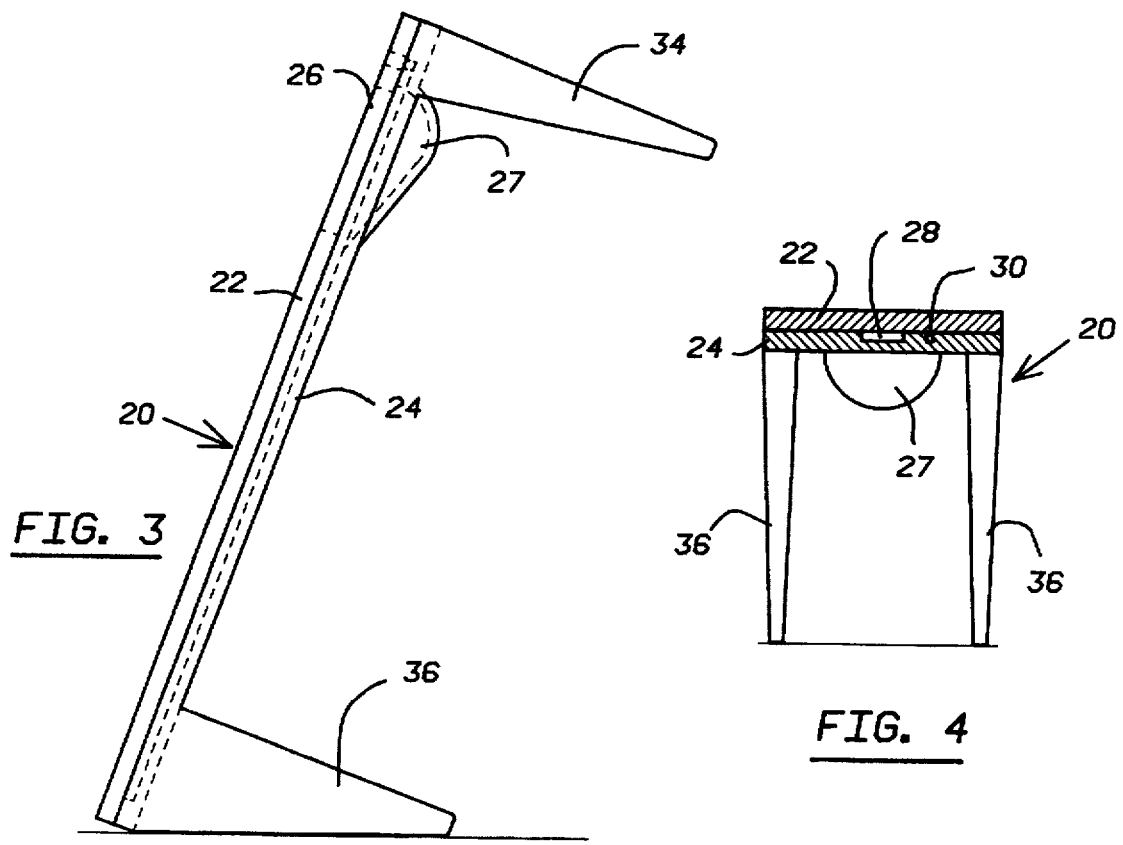
FIG. 3
FIG. 4

DEVICE FOR ANALYSIS OF RAPID AGGLUTINATION OF PARTICLES AND METHOD FOR USING SAME

This application is a continuation of application Ser. No. 07/818,410, filed Jan. 3, 1992, now abandoned, which is a continuation of application Ser. No. 07/572,519, filed Aug. 23, 1990, now abandoned.

BACKGROUND OF THE INVENTION

This invention relates generally to a device useful for the analysis of the rapid agglutination of particles, and more particularly, relates to a device useful in the evaluation of analytes attached to the surfaces of particles. The device also is particularly useful for the evaluation of analytes in a liquid through the use of particles coated with a binding agent specific for that analyte.

Numerous attempts have been made to create devices for analysis of particles or sediment in a liquid test sample. For example, U.S. Pat. No. 4,441,793 to Eikens teaches a device with a flat viewing area between 0.15 and 3.0 mm, with sidewalls extending from a base which completely surrounds the circular viewing area. U.S. Pat. No. 3,777,283, also to Eikens, describes a device wherein sidewalls diverge slightly toward an open side of the device.

U.S. Pat. No. 4,088,448 to Lilja teaches a device which requires that the mixing of reagents be performed by rocking or vibration in order to form a reaction by capillary action. Similarly, U.S. Pat. No. 3,961,346 to White describes a capillary chamber formed by slightly inwardly curving walls in which particle motion is obtained by external interaction. U.S. Pat. No. 4,447,140 to Campbell teaches the use of a spacing means of film or a plurality of filaments which define a series of chambers. However, leakage can occur between chambers. U.S. Pat. No. 4,022,521 to Hall describes a device having microprojections which allow for the free flow of fluid in all directions.

These described devices, however, do not sufficiently provide the particle interaction necessary for the detection of low levels of analyte without additional external motion being imparted to the chamber to cause the reaction. Thus, these devices are better suited for the observation of stationary substances.

Other devices rely on capillary action to fill the chamber, which filling occurs immediately when fluid is added to the receiving region of the device. For example, U.S. Pat. No. 4,596,695 to Cottingham teaches such a device wherein two panels are separated by a spacer means, such as silk screening, ink, film or dust. U.S. Pat. No. 4,774,515, also to Cottingham, teaches another device wherein the channel of the device has greater length than the total length of the panel.

U.S. Pat. No. 4,323,536 to Columbus teaches a device wherein a distance between two surfaces is necessary to induce capillary flow. This device also includes a temporary energy barrier, and means for preventing introduced liquid from flowing onto test elements until the non-test area is completely wet.

U.S. Pat. No. 4,756,884 to Hillman et al. describes a device containing five units connected in a "continuous capillary pathway," wherein variations in flow rate occur due to the reagents used. U.S. Pat. No. 4,790,640 to Nason teaches a device that uses a bonding agent which includes an ink layer of predetermined thickness which layer defines chambers in the device. The spacing between the top and bottom of the device is small enough to draw liquid by capillary action.

These described devices, however, do not allow for the addition of multiple reagents in succession, or for a pre-incubation step in the device. Such manipulations must be performed in a separate vessel and then added to the device. Theoretically, the particles collide as the fluid moves through the chamber, allowing for the formation of agglutinates. To a large extent, this formation of agglutinates is affected by the rate at which the reaction mixture moves through the device. The formation of agglutinates ceases when the flow of the mixture stops, thus ending the collision of particles. Variation in flow rates between multiple capillary devices due to, for example, the leaching of plasticizers found in injection molded plastic devices, wetting agents and detergent additives in reagents, and viscosity differences between different sample and reagents types, often can lead to irreproducible results.

It therefore would be advantageous to provide a device which requires no external interaction once placed in an operating mode, and which promotes particle interaction while requiring no external interaction, such as shaking, to fill the chamber with the reaction mixture. Such a device also could enhance particle interaction and achieve rapid agglutination. Such a device would be useful for the evaluation of analytes attached to the surface of particles, or the evaluation of analytes in a test sample, through the use of particles coated with a binding agent specific for the analyte of interest. The device preferably would be inexpensive to manufacture yet provide the end user with reproducible results.

SUMMARY OF THE INVENTION

The present invention provides a device for particle agglutination analysis which comprises a means forming a longitudinally extending channel, an opening which communicates from the exterior of the device to the first end of the channel, a reservoir which communicates with the second end of the channel, and a vent opening communicating from the reservoir to the exterior of the device. The channel has sufficiently large cross section and the vent is so positioned that, when the channel is in a vertical position, a given amount of fluid, which is introduced through the opening into the channel, will flow by gravity through the channel and into the reservoir, filling the channel to a desired height and the reservoir to the same height without flowing through the vent. Air that was originally in the channel and in the reservoir escapes through the vent. The opening has a sufficiently large volume such that the given volume of fluid can be introduced into the opening when the device is in such a position that the channel extends horizontally with the opening facing upwardly, and will fill the channel to the desired height and the reservoir to the same height, when the device is placed at an angle to the horizontal such that the channel extends vertically with the opening at the top. The opening communicating with the first end of the channel is a receiving well, which is a non-test area and which accommodates the addition of fluids to the device placed at the horizontal without leakage of these fluids from a non-test area into the test area and reservoir. Fluid passes rapidly to the test area and reservoir upon placing the device at an angle to the horizontal. At this point, agglutination begins to occur. The device also can include a support which is operable when placed on a substantially horizontal surface, which supports the device with the channel positioned such that, when the channel contains a reaction mixture comprising a test sample and particles, gravity will cause sufficient movement of the particles in the channel over a sufficient period of time to cause agglutination of the particles. A second support also can be included to support the device when the channel extends generally horizontally and the opening faces upwardly. The channel can extend at an angle of about 45 to about 85 degrees to the horizontal. More preferably, the channel will extend at an angle of about 60 to about 80 degrees to the horizontal. The most preferred angle at which the channel can extend is 70 degrees.

A method for using a device for particle agglutination analysis also is provided. The method comprises adding a reaction mixture suspected of containing an analyte of interest, a capture reagent specific for the analyte and a diluent to the receiving well of a device with the channel extending generally horizontally and the opening facing upwardly, placing the device at an angle to the horizontal with the opening at the top, thus introducing the suspension into the longitudinally extending channel such that gravity will cause sufficient movement of the suspension to cause agglutination of the particles if the test sample contains more than a low threshold amount of the analyte, and examining the channel to determine whether or not agglutination has occurred.

BRIEF DESCRIPTION OF THE DRAWINGS

FIG. 1 is a top view of the device, demonstrating a single flow channel.

FIG. 2 is a longitudinal cross-sectional view of FIG. 1 taken along line 40—40.

FIG. 3 is a longitudinal side view of FIG. 1 demonstrating the device standing at an angle to the horizontal.

FIG. 4 is a lateral cross-sectional view of FIG. 1 taken along line 42—42.

DETAILED DESCRIPTION OF THE INVENTION

Figure 5:
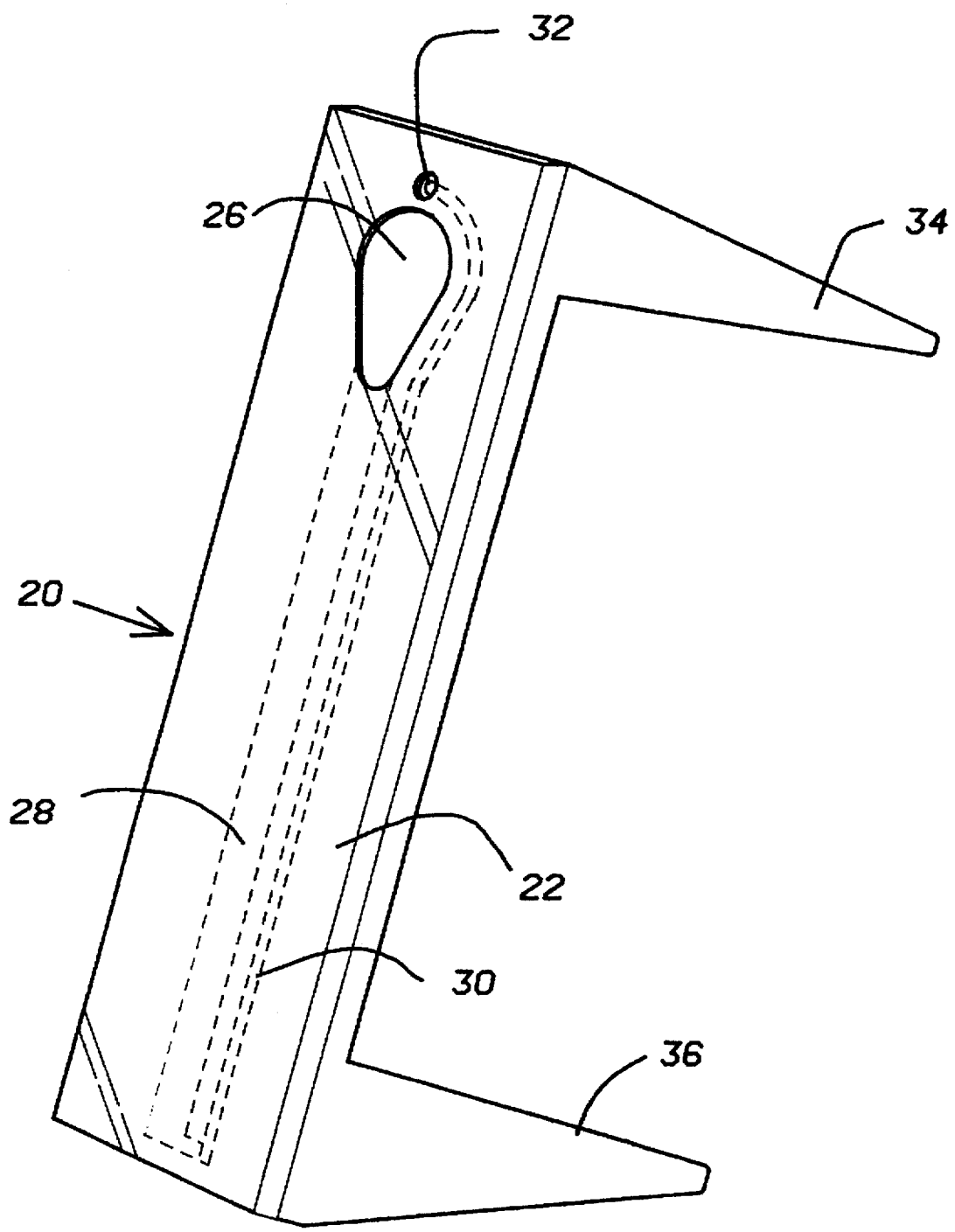
FIG. 5 is a perspective view of FIG. 1.

This invention provides a device for particle agglutination and a method for use of this device. The device includes a receiving well, a reaction chamber, and a reservoir, to control mixing and containment of reagents both before and after the device is placed in an operating mode, and to determine whether agglutination has occurred. In the present invention, the particle interaction leading to agglutination occurs after the particle suspension fills the device, regardless of the presence of substances which may affect flow rate. The present invention is self-sufficient in that the receiving well can accommodate reagents added in succession, or that require a pre-incubation step before addition of another reagent, and the reaction mixture will not enter the chamber until the device is placed in the operating mode.

The present invention can be utilized to perform immunoassays, although the present invention is not limited to immunoreactive assays. Any assay utilizing specific binding members can be performed. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal, and complexes thereof, including those formed by recombinant DNA methods.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of naturally occurring specific binding partners (pairs) such as the use of intrinsic factor protein as a member of a specific binding pair for the determination of Vitamin B12, or the use of a lectin as a member of a specific binding pair for the determination of a carbohydrate. The analyte can include a protein, a peptide, an amino acid, a hormone, a steroid, a vitamin, a drug including those administered for therapeutic purposes as well as those administered for illicit purposes, a bacterium, a virus, and metabolites of or antibodies to any of the above substances. The details for the preparation of such antibodies and the suitability for use as specific binding members are well known to those skilled in the art.

The "test sample" can be a sample of biological fluid, such as serum, plasma, ascites, urine, cerebral spinal fluid and the like; cellular components of the body such as white or red blood cells; and other constituents of the body which may contain the analyte of interest. Optionally, test samples may be obtained from water, soil, and vegetation.

The reaction mixture added to the receiving well of the present invention may comprise a test sample containing the analyte of interest, possibly diluted in a sample diluent, which will be combined with a particle suspension where the particles are coated with a capture reagent specific for the analyte of interest. The reaction mixture also can comprise a test sample containing an analyte of interest attached to the surface of the particles, possibly diluted in a sample diluent, which will be combined with a solubilized capture or binding agent specific for that analyte.

The capture reagents of the present invention comprise specific binding member of the analyte of interest which is attached to the solid phase. This attachment can be achieved, for example, by coating the specific binding member onto the solid phase by absorption or covalent coupling. Coating methods, and other known means of attachment, are known to those of ordinary skill in the art.

The specific binding member of the capture reagent can be any molecule capable of specifically binding with another molecule. The specific binding member of the capture reagent can be an immunoreactive compound such as an antibody, antigen or antibody/antigen complex. If an antibody is used, it can be a monoclonal antibody, a polyclonal antibody, an antibody fragment, a recombinant antibody, a mixture thereof, or a mixture of an antibody and other specific binding members.

The solid phase particles can be selected by one skilled in the art. Thus, latex particles, red blood cells, aldehyde-fixed red blood cells, yeast, bacteria, aldehyde-fixed yeast or bacteria, and gelatin can be utilized. The particles may range in size from about 0.3 to about 10 microns in diameter. It has been determined that particles which are greater than about 10 microns in diameter render the visual observation of agglutination difficult. Those skilled in the art will recognize the scope of methodologies which may be applied relative to the application of useful solid phases.

In a preferred form of the invention, the device consists of two subassemblies comprising the flow chamber and the cover. The two subassemblies are molded from optically transparent plastic. The flow channel is formed when the subassemblies are attached to each other by ultrasonic welding. The flow channel comprises an opening or sample port communicating from the exterior of the cover at the first end of the channel to the receiving well, which communicates with a reaction chamber, communicating with a reservoir, with a vent opening communicating from the reservoir to the exterior of the device at the second end of the channel. When the device is placed in an operating mode, the channel is positioned so that its axis extends at a 70 degree angle to the horizontal. Gravity will cause sufficient movement of the particles to effect agglutination if the analyte of interest is present in a sufficient amount. After the completion of an incubation period, for example, 20 minutes, the device may be restored to the horizontal. Restoring the device to the horizontal provides stability of the test result and the opportunity for documentation. The operation of the present invention does not require the use of expensive equipment, and therefore may lend itself to analytical testing in non-laboratory settings.

The sufficient amount of analyte detectable by the present invention is approximately 100 to 200 picograms (pg) of analyte per 20 microliter (µL) of test sample. It will be appreciated that the sensitivity and specificity of detection of analytes will vary depending on the analyte being assayed and the assay reagents utilized. Those skilled in the art will realize that variations in reagents such as the choice of capture reagents, solid phase particles, and diluents, as well as the volume of test sample, all influence the sensitivity and specificity of individual assays, and these obvious variations are intended to be included in the scope of the present invention.

Referring to the figures, the device indicated generally at 20 in FIGS. 1 through 5 comprises a base member 24 and a cover sheet 22. As seen in FIGS. 1 and 2, the base member 24 has positioning legs 34 and 36 at each of the four corners, a longitudinally extending channel 28, a reservoir 30, and a receiving well 27 (as seen in FIG. 2). The cover sheet 22 is welded to the base member 24, and has a relatively large diameter hole 26 and a relatively small hole 32 at its upper end (as seen in FIG. 5). The large diameter hole 26 is aligned with the receiving well 27, and the small diameter hole or vent 32 is aligned with the terminal end of the reservoir 30. The positioning legs 34 and 36 serve as supports for the device 20 when it is placed upon a horizontal surface, so that the channel 28 extends horizontally (as seen in FIG. 2) or at an angle to the horizontal (as seen in FIG. 3).

When the positioning legs 34 and 36 of the device 20 rest on a horizontal surface, a reaction mixture comprising a test sample suspected of containing an analyte and which reaction mixture may or may not comprise a particle suspension, a binding agent specific for that analyte and which binding agent may or may not comprise a particle suspension, and a diluent, can be added to the receiving well 27, and the device 20 then is positioned such that the axis of the channel which contains the reaction mixture is inclined at an angle of about 70° to the horizontal such that the receiving well 27 is at the top. With the device 20 in this position, all the reaction mixture will flow from the receiving well 27 into the adjacent channel 28, with excess reaction mixture flowing into the reservoir 30. Only the air present in the channel 28 and reservoir 30, and not the reaction mixture that is present in the channel 28 and reservoir 30, escapes through the vent 32. The volume of reaction mixture can comprise an approximately 40 to 135 µL quantity of reaction mixture; preferably, the volume utilized is approximately 60 µL of reaction mixture. The reaction mixture enters the reservoir 30 and balances the column of reaction mixture in the channel 28. If the test sample suspected of containing an analyte contains a sufficient amount of the analyte, agglutination occurs in about 20 minutes.

Figure 7:
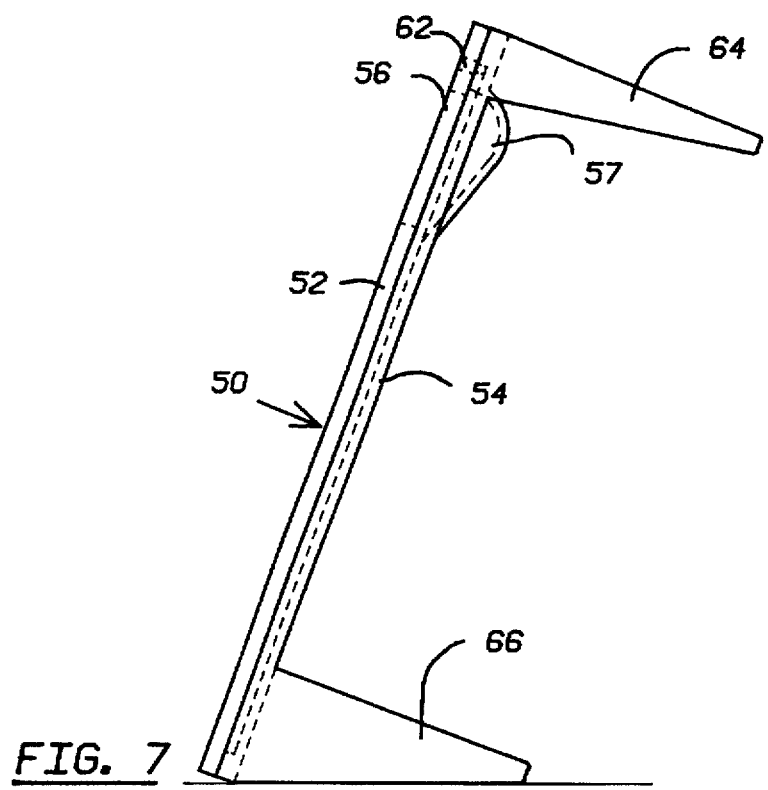
FIG. 7 is a longitudinal side view of FIG. 6.
Figure 6:
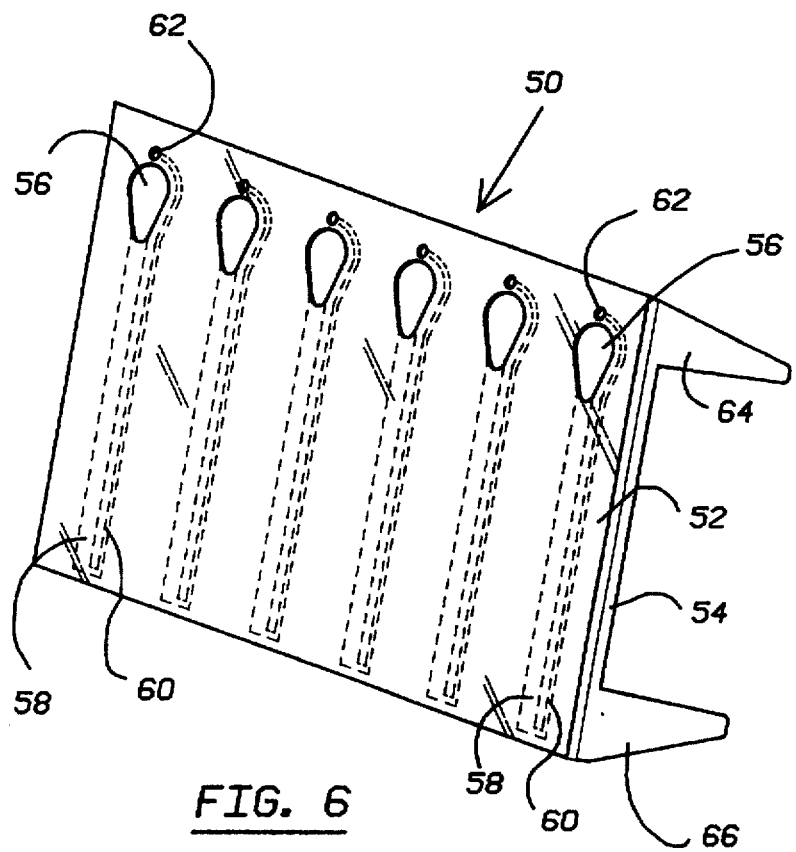
FIG. 6 is a perspective view of the device, demonstrating multiple parallel flow channels in a single unit.

Referring to FIGS. 6 and 7, the device indicated generally at 50 comprises a base member 54 and a cover sheet 52. The base member 24 has positioning legs 64 and 66 at each of the four corners, a plurality of parallel longitudinally extending channels 58, reservoirs 60, and receiving wells 57. The cover sheet 52 is welded to the base member 54, and has relatively large diameter holes 56 and relatively small diameter holes 62 at its upper end (as seen in FIG. 6). The large diameter holes 56 are aligned with the receiving wells 57, and the small diameter holes or vents 62 are aligned with the terminal end of the reservoirs 60. The positioning legs 64 and 66 serve as supports for the device 50 when it is placed upon a horizontal surface, so that the channels 58 extend either horizontally or at an angle to the horizontal (as seen in FIG. 7).

When the positioning legs 64 and 66 of the device 50 rest on a horizontal surface, a reaction mixture comprising a test sample suspected of containing an analyte and which reaction mixture may or may not comprise a particle suspension, a binding agent specific for that analyte and which binding agent may or may not comprise a particle suspension, and a diluent, can be added to the receiving wells 57, and the device 50 then is positioned such that the axis of the channels which contain the reaction mixtures is inclined at an angle of about 70° to the horizontal, such that the receiving wells 57 are at the top. With the device 50 in this position, all the reaction mixtures will flow from the receiving wells 57 into the adjacent channels 58, with excess reaction mixtures flowing into the reservoirs 60. Only the air present in the channels 58 and reservoirs 60, and not the reaction mixtures that are present in the channels 58 and reservoirs 60, escape through the vents 62. The volume of reaction mixture can comprise an approximately 40 to 135 µL quantity of reaction mixture; preferably, the volume utilized is approximately 60 µL. The reaction mixtures enter the reservoirs 60 and balance the columns of reaction mixtures in the channels 58. The plurality of channels 58 of the device 50 allow for the simultaneous evaluation of multiple test samples suspected of containing a single analyte, or for the simultaneous determination of the presence, if any, of multiple analytes suspected of being present in a single test sample. If the test sample contains a sufficient amount of the analyte, agglutination will occur in about 20 minutes.

Figure 9:
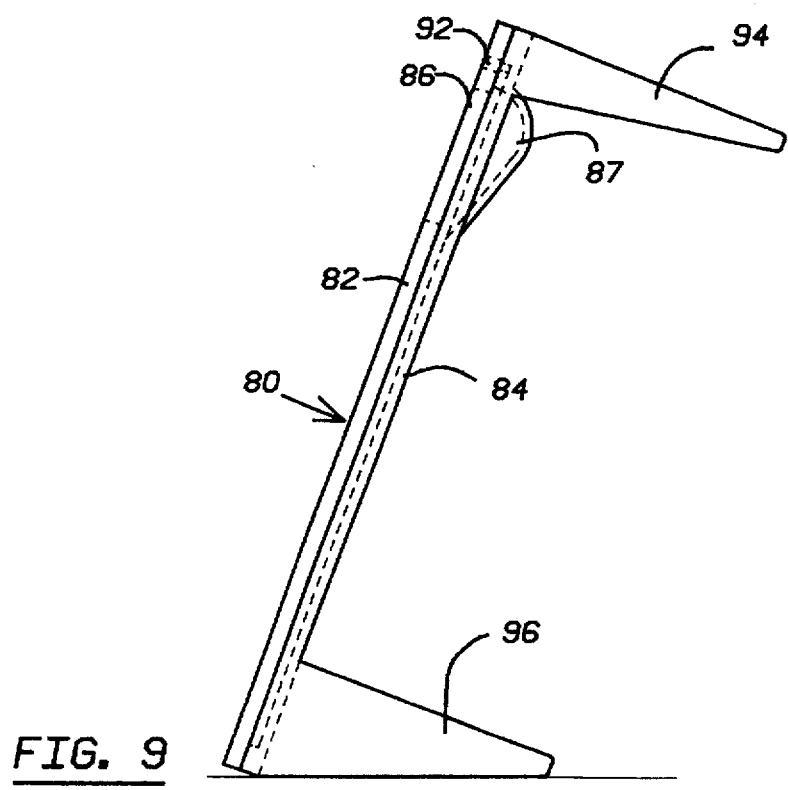
FIG. 9 is a longitudinal side view of FIG. 8.
Figure 8:
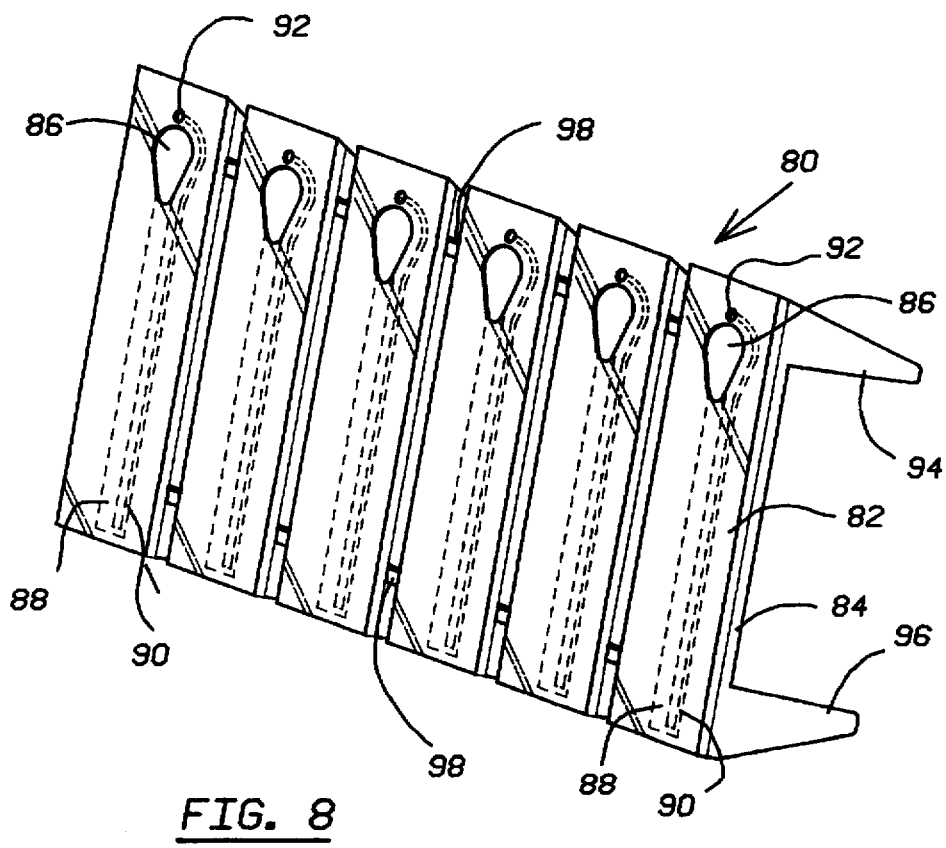
FIG. 8 is a perspective view of the device demonstrating multiple parallel flow channels in a single unit, connected by frangible plastic tabs.

Referring to FIGS. 8 and 9, the device indicated generally at 80 comprises a base member 84 and a cover sheet 82. The base member 84 has positioning legs 94 and 96 at each of the four corners, a plurality of parallel longitudinally extending channels 88, reservoirs 90, and receiving wells 87. The cover sheet 82 is welded to the base member 84, and has relatively large diameter holes 86 and relatively small diameter holes 92 at its upper end (as seen in FIG. 8). The large diameter holes 86 are aligned with the receiving wells 87, and the small diameter holes or vents 92 are aligned with the terminal end of the reservoirs 90. The positioning legs 94 and 96 serve as supports for the device 80 when it is placed upon a horizontal surface, so that the channels 88 extend either horizontally or at an angle to the horizontal (as seen in FIG. 8).

The plurality of channels 88 of the device 80 may be separated by breaking the frangible plastic tabs 98, splitting the plurality of channels 88 into a desired quantity of subsets or individual units depending on quantity of test samples to be evaluated.

When the positioning legs 94 and 96 of the device 80 rest on a horizontal surface, a reaction mixture(s) comprising a test sample suspected of containing an analyte and which reaction mixture(s) may or may not comprise a particle suspension, a binding agent specific for that analyte and which binding agent may or may not comprise a particle suspension, and a diluent, can be added to the receiving well(s) 87. The device 80 then is positioned such that the axis of the channel which contains the reaction mixture(s) is inclined at an angle of about 70° to the horizontal, such that the receiving well(s) 87 is at the top. With the device 80 in this position, all the reaction mixture(s) will flow from the receiving well(s) 87 into the adjacent channel(s) 88, with excess reaction mixture(s) flowing into the reservoir(s) 90. Only the air present in the channel(s) 88 and the reservoir(s) (90), and not the reaction mixture(s) that is in the channel(s) 88 and reservoir(s) 90 escapes through the vent(s) 92. The volume of reaction mixture can comprise an approximately 40 to 135 µL quantity of reaction mixture; preferably, the volume utilized is approximately 60 µL. The reaction mixture(s) enters the reservoir(s) 90 and balances the column(s) of reaction mixture(s) in the channel(s) 88. The plurality of channels 88 of the device 80 allow for the simultaneous evaluation of multiple test samples suspected of containing a single analyte of interest, or the simultaneous detection of the presence, if any, of multiple analytes from a single test sample suspected of containing multiple analytes of interest. If the test sample contains a sufficient amount of the analyte(s), agglutination will occur in about 20 minutes.

The present invention will be more fully understood from the following examples, which are presented solely for the purpose of illustration, and are not to be construed as limiting the present invention.

As used herein, the terms "percent" and "parts" refer to percent and parts by volume unless otherwise indicated. "g" means gram(s); "mg" means milligram(s); "ng" means nanogram(s); "L" means liter(s); "mL" means milliliter(s); "µL" means microliter(s); and "v/v" means percent by volume.

EXAMPLE 1

The device 20 shown in FIG. 1 was used to conduct particle agglutination assays with samples of normal human serum into which varying amounts of recombinant hepatitis B surface antigen had been spiked. The spiked samples contained 5700, 570, 285, 143, 71, 36, 18 and 0 ng per mL of recombinant hepatitis B surface antigen. A reaction mixture comprising a test sample and coated particles was obtained by mixing one part of the sample which contained 5700 ng per mL recombinant hepatitis B surface antigen with two parts by volume of a 7 v/v suspension of aldehyde fixed red blood cells that had been coated with polyclonal antibody to hepatitis B surface antigen and suspended in a sample diluent. A 60 µL volume of reaction mixture was introduced to the device 20, which then was supported so that channel 28 extended at an angle of 70° to the horizontal. Twenty minutes later, large agglutinates with a clear background were seen by visual observation.

The aldehyde fixed red blood cells used as described above in Example 1 were those which are commercially available from Abbott Laboratories (Abbott Park, Ill.) under the designation DURACYTE®. The sample diluent used was that which is commercially available from Abbott Laboratories (Abbott Park, Ill.) under the designation RUBACELL®.

EXAMPLE 2

The procedure described by Example 1 was repeated to test the other spiked samples identified in Example 1 when the channel 28 was 70 degrees to the horizontal. Further, all of the spiked samples described in Example 1 were tested following the procedure of Example 1 when the channel 28 was horizontal, when it extended at 45° to the horizontal, and when it extended at 90° to the horizontal. The results obtained by this testing are set forth in Table 1, where 3+ means "large sized agglutinates-clear background", 2+ means "medium sized agglutinates-clear background", 1+ means "small sized agglutinates-turbid background", + means "very fine agglutination", and − means "homogeneous particle suspension".

TABLE 1

| Channel 28 | Recombinant hepatits B surface antigen (ng per mL) | | | | | | | |
|---|---|---|---|---|---|---|---|---|
| Angle | 5700 | 570 | 285 | 143 | 71 | 36 | 18 | 0 |
| 0° | 1+ | + | − | − | − | − | − | − |
| 45° | 1+/2+ | 1+/2+ | 1+/2+ | 1+/2+ | 1+/2+ | 1+ | 1+ | − |
| 70° | 3+ | 2+/3+ | 2+/3+ | 2+ | 1+/2+ | 1+ | + | − |
| 90° | 3+ | 2+ | 1+ | + | − | − | − | − |

It will be appreciated from the foregoing data that the agglutination procedures of Examples 1 and 2 are capable of detecting extremely small quantities of the recombinant hepatitis B surface antigen and require only a short incubation time. When the channel was inclined at 45° to the horizontal, detection of the same extremely small quantity of antigen was still possible. However, the appearance of the agglutinated sample was less desirable because it was more difficult to detect by visual observation. It was found that incubation at an angle of 45° to the horizontal was easier to detect by visual observation after a longer period of incubation, for example, 60 minutes. Therefore, while an angle of 45° is operable and is significantly superior to incubation with the channel 28 in either the horizontal or vertical position, a greater inclination is preferred.

EXAMPLE 3

The relationship between the position of the channel 28 and the results of the assay were investigated further by the procedure described in Example 2 with the channel inclined at 40°, 50°, 60°, 70°, 80°, and 85° to the horizontal. The results of these assays are set forth in the following Table 2, wherein the meanings of the numerical designations are those as described for Table 1.

TABLE 2

| Channel 28 | Recombinant hepatitis B surface antigen (ng per mL) | | | | | | | |
|---|---|---|---|---|---|---|---|---|
| Angle | 5700 | 570 | 285 | 143 | 71 | 36 | 18 | 0 |
| 40° | 1+ | 1+ | 1+ | 1+ | 1+ | 1+ | + | − |
| 50° | 2+ | 2+ | 2+ | 1+/2+ | 1+/2+ | 1+ | + | − |
| 60° | 2+/3+ | 2+/3+ | 2+/3+ | 2+ | 1+/2+ | 1+ | + | − |
| 70° | 3+ | 3+ | 2+/3+ | 2+ | 1+ | 1+ | + | − |
| 80° | 3+ | 3+ | 2+/3+ | 2+ | 1+ | + | − | − |
| 85° | 3+ | 2+ | 1+/2+ | 1+ | + | − | − | − |

After the readings reported in Table 2 were taken, the samples were left in the indicated positions and were examined again after one hour (40 additional minutes) of incubation. After this additional incubation, the 18 ng per mL samples showed very fine agglutination ("+") in the channels 28 positioned at 80° and 85° to the horizontal. When the channel 28 was positioned at 40°, it was more difficult to determine agglutination than when the channel was positioned at 50° through 85°. Thus, the device 20 provides acceptable results when it is inclined at an angle of from about 40° to about 85° to the horizontal. A preferred range of angles is from about 60° to about 80° to the horizontal. For optimum results, considering both the speed of agglutination and the ease of making a visual determination of agglutination, the preferred angle is about 70° to the horizontal.

It will be appreciated that changing the parameters of a particle agglutination assay, e.g., by substituting another binding agent for the aldehyde fixed red blood cells that had been coated with antibody to hepatitis B surface antigen used in the foregoing procedures, may change the relationships between the angle of the device 20 and the assay results, and that these relationships may be different if either the dimensions or the material of construction of the device 20 are changed. All presently available results indicate that an angle between 40° and 85° is operable. In any event, if any given agglutination assay is to be conducted in accordance with the method of the instant invention in a small diameter channel having a cross section sufficiently large that flow is by gravity, essentially the procedures described above as having provided the data for the foregoing tables can be carried out, and ease of reading and minimum detectable analyte concentration can be determined as a function of angle of the channel. Subsequent assays then can be conducted with the channel positioned at an angle to the horizontal selected on the basis of the results obtained.

It will be apparent that various changes and modifications can be made from the details of the invention as described herein and as shown in the attached drawings without departing from the spirit and scope of the attached claims.

We claim:

1. An agglutination assay for detecting the presence or amount of an analyte in a test sample, comprising the steps of:
   a) placing the test sample in a device comprising:
      i) a sample receiving well which accommodates the test sample when the device is in a horizontal position,
      ii) a reaction chamber having a first end and a second end, wherein said receiving well communicates with said first end of said reaction chamber such that the test sample passes from said receiving well and fills said reaction chamber when the device is placed at an angle to the horizontal but will not pass when the device is horizontal,
      iii) a reservoir communicating with said second end of said reaction chamber to collect excess test sample from said reaction chamber,
      iv) a vent communicating from said reservoir to the exterior of the device; and
   b) placing the device at an angle to the horizontal, thereby initiating an agglutination reaction between a suspension of particles and the analyte whereby gravity causes the downward movement of said particles through said filled reaction chamber to cause agglutination if the analyte is present at a threshold amount; and
   c) observing the agglutination reaction which occurs in said reaction chamber in the presence of analyte.

2. The assay according to claim 1, further comprising the step of incubating the test sample with a particle suspension in said receiving well while the device is in a horizontal position.

3. The assay according to claim 1, wherein the device is placed at an angle of about 45° to about 85° to the horizontal.

4. The assay according to claim 1, wherein the device is placed at an angle of about 60° to about 80° to the horizontal.

5. The assay according to claim 1, wherein the device is placed at an angle of about 70° to the horizontal.

6. An agglutination assay device for detecting the presence or amount of an analyte in a test sample, comprising:
   a) a sample receiving well which accommodates the test sample when the device is in a horizontal position;
   b) a reaction chamber having a first end and a second end, wherein said receiving well communicates with said first end of said reaction chamber such that the test sample passes from said receiving well and fills said reaction chamber when the device is placed at an angle to the horizontal but will not pass when the device is horizontal,
   thereby initiating an agglutination reaction between a suspension of particles and the analyte whereby causes the downward movement of said particles through said reaction chamber to cause agglutination if the analyte is present at a threshold amount,
   c) a reservoir communicating with said second end of said reaction chamber to collect excess test sample from said reaction chamber, and
   d) a vent communicating from said reservoir to the exterior of the device, further comprising a support means which is operable to place the device at an angle to the horizontal,
   wherein said support means is operable to place the device at an angle of about 45° to about 85° to the horizontal.

7. The device according to claim 6, wherein said support means is operable to place the device at an angle of about 60° to about 80° to the horizontal.

8. The device according to claim 6, wherein said support means is operable to place the device at an angle of about 70° to the horizontal.

* * * * *

UNITED STATES PATENT AND TRADEMARK OFFICE
CERTIFICATE OF CORRECTION

PATENT NO. : 5,702,953
DATED : December 30, 1997
INVENTOR(S) : Mazurek et al.

It is certified that error appears in the above-identified patent and that said Letters Patent is hereby corrected as shown below:

Column 10, line 41, after "whereby" insert --gravity--

Column 10, line 47, change "," to --;--.

Signed and Sealed this

Twelfth Day of January, 1999

Attest:

Attesting Officer

*Acting Commissioner of Patents and Trademarks*